United States Patent
Peck et al.

(10) Patent No.: US 7,507,534 B2
(45) Date of Patent: Mar. 24, 2009

(54) RAPID EFFICACY ASSESSMENT METHOD FOR LUNG CANCER THERAPY

(75) Inventors: Konan Peck, Taipei (TW); Yuh-Pyng Sher, Taipei (TW); Jin-Yuan Shih, Taipei (TW); Pan-Chyr Yang, Taipei (TW); Cheng-Wen Wu, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 11/306,532

(22) Filed: Dec. 31, 2005

(65) Prior Publication Data

US 2007/0048750 A1    Mar. 1, 2007

Related U.S. Application Data

(60) Provisional application No. 60/596,104, filed on Sep. 1, 2005.

(51) Int. Cl.
*C12Q 1/68*    (2006.01)
(52) U.S. Cl. .......................................... 435/6
(58) Field of Classification Search ................. 435/6
See application file for complete search history.

(56) References Cited

U.S. PATENT DOCUMENTS

2004/0053317 A1* 3/2004 Glinskii ................. 435/6
2004/0191819 A1* 9/2004 Eveleigh et al. ............ 435/6

FOREIGN PATENT DOCUMENTS

WO    WO2004/076643    9/2004

OTHER PUBLICATIONS

Tockman et al (Cancer Res., 1992, 52:2711s-2718s).*
Peck et al (Jul. 1998, Cancer Research, 58:2761-2765).*
Fleischhacker et al (Sep. 2001, Ann NY Acad Sci, 945:179-188).*
Tockman et al (Cancer Res., 1992, 52:2711s-2718s).*
McDoniels-Silvers et al (Clinical Cancer Research, Apr. 2002, 8:1127-1138).*
Peck et al. Detection and quantitation of circulating cancer cells in the peripheral blood of lung cancer patients. Cancer Research, 58:2761-2765, Jul. 1, 1998.
Yamashita et al. Preoperative evidence of circulating tumor cells by means of reverse transcriptase-PCR for carcinoembryonic antigen messenger RNA is an Independent predictor of survival in non-small cell lung cancer: a prospective study. J Thorac Cardiovasc Surg, 124:299-305, 2002.
Keilholz et al. Quantitative detection of circulating tumor cells in cutaneous and ocular melanoma and quality assessment by real-time reverse trascriptase-polymerase chain reaction. Clinical Cancer Research, 10:1605-1612, Mar. 1, 2004.
Hoon et al. Detection of occult melanoma cells in blood with a multiple-marker polymerase chain reaction assay. Journal of Clinical Oncology, 13:2109-2116, Aug. 1995.
Taback et al. Detection of occult metastatic breast cancer cells in blood by a multimolecular marker assay: correlation with clinical stage of disease. Cancer Research, 61:8845-8850, Dec. 15, 2001.

* cited by examiner

*Primary Examiner*—Sean E Aeder
(74) *Attorney, Agent, or Firm*—Occhiuti Rohlicek & Tsao LLP

(57) ABSTRACT

The present invention discloses a method for rapid assessment of lung cancer therapy efficacy in a few days instead of weeks by conventional imaging methods. This method can also be used to detect relapse of the cancer and to improve the current TNM cancer staging method for more accurate prognosis. The rapid assessment of therapy efficacy is based on detecting circulating cancer cells in body fluid with high positive detection rate. The high positive detection rate is achieved by using qPCR amplification of multiple marker genes identified by in silico search of DNA sequence database. This invention also discloses a scoring method to calculate the cancer cell load based on qPCR results to correlate the amount of circulating cancer cells in lung cancer patients and predict the treatment outcomes.

2 Claims, 4 Drawing Sheets

RAPID EFFICACY ASSESSMENT METHOD FOR LUNG CANCER THERAPY

CROSS-REFERENCE TO RELATED APPLICATIONS

This application claims the benefit of U.S. Provisional Application No. 60/596,104, filed Sep. 1, 2005, which is incorporated herein by reference.

BACKGROUND OF THE INVENTION

1. Field of the Invention

The present invention relates generally to methods for assessment of carcinoma cancer therapy and relapse detection, and more specifically it relates to an efficacy assessment method for lung cancer therapy to rapidly predict the outcome of lung cancer therapy so treatment with higher likelihood of success can be selected to prevent invalid treatment from wrecking patents, and a routine monitoring method for cancer relapse after the treatment.

2. Description of the Related Art

Lung cancer is the leading cause of cancer-related death and non-small cell lung cancer (NSCLC) accounts for ~80% of the cases. Attempts to use serum protein markers for the early diagnosis of lung cancer have not yielded satisfactory results for routine screening, and newly developed early diagnostic methods using serum DNA as a diagnostic marker await further validation. Current therapeutic measures remain unable to lower the mortality rate of late-stage lung cancer patients. Surgical resection is still the best cure for the early-stage patients. The tumor, node, metastasis (TNM) classification has been used for cancer staging and prognosis for decades. A large portion of early-stage patients, defined by the current staging system and available imaging modalities, still develop distant metastases although they received surgical removal of the tumor mass. The inability to detect disseminated tumor cells with the current imaging techniques is a major obstacle to accurate cancer staging.

NSCLC is heterogeneous with respect to histology and biological characteristics. Individual NSCLC cells within a tumor and in different patients' tumors express different amounts of marker gene transcripts. The heterogeneity of marker gene expression levels in NSCLC cells limits the reliability of an assay method with a single-marker detection scheme. Several literature reports have described PCR methods for the detection of tumor cells dispersed in the circulation. However, not one tumor marker is consistently and specifically expressed in all of the primary tumors of a particular malignancy. Literature reports have also shown that a panel of marker genes provides a more reliable and informative approach than a single-marker assay for the detection of melanoma and breast cancer cells in blood. Such assays for lung cancer have been limited by the availability of molecular markers.

The presence of epithelial cancer cells in the bone marrow and in the peripheral blood of patients with carcinoma has been reported in literature reports and prior arts. In contrast to bone marrow aspirates, peripheral blood samples can be obtained routinely and more readily. Carcinoma accounts for around 85% of human cancers and the carcinoma cells are of epithelial cell lineage. Techniques such as immunocytology and flow cytometry have been employed in prior arts to detect circulating cancer cells in the peripheral blood. However, both techniques are based on extracting or labeling intact carcinoma cells in circulation by antibodies targeting specifically to the epithelial cell surface antigens such as EpCAM and others. Malignant carcinoma cancer cells often are de-differentiated and lose the characteristic epithelial cell surface antigens. In addition, it is known in cancer research field that EpCAM gene expression is often suppressed to facilitate tumor metastasis. Therefore, the antibody based detection methods have been reported to have low positive detection rates or high false negative rates. Polymerase chain reaction (PCR) has been employed to detect disseminated tumor cells in peripheral blood. Several literature reports have described the use of PCR for detecting circulating cancer cells in the peripheral blood of patients of various cancers. For instance, Peck et al., reported the use of cytokeratin 19 as the maker gene for detecting circulating cancer cells in NSCLC patients with an overall positive detection rate around 40%.

Compared with immunocytology and flow cytometry, PCR has the advantages that it is more readily available, less involved in the operating procedures, less instrument cost, and others. On the other hand, PCR is not able to yield the number of counts of circulating cancer cell in a sample like the other two techniques.

To overcome the current technology difficulties in achieving high positive detection rate and rapid assessment of lung cancer therapy efficacy and relapse detection, a panel of marker genes for achieving high positive detection rate by qPCR and a quantitative analysis method for predicting lung cancer treatment outcome and for prognosis are needed.

SUMMARY OF THE INVENTION

The present invention fulfills the needs in lung cancer treatment by teaching a rapid efficacy assessment method for lung cancer therapy and relapse detection.

The purpose of the present invention is to teach an assessment method for lung cancer therapy. More especially, it teaches a rapid efficacy assessment method for lung cancer therapy by identifying and employing a panel of marker genes for real-time quantitative PCR (qPCR) assay to quantitatively measure the amount of circulating lung cancer cells in body fluids.

Another purpose of the present method is to teach a method for cancer relapse detection by using real time qPCR with a panel of marker genes for detecting circulating lung cancer cells in body fluids.

The present invention identifies a panel of markers for the detection of circulating cancer cells in NSCLC patients by in silico analysis of the National Cancer Institute-Cancer Genome Anatomy Project database. The present invention also teaches a quantitative analysis method to calculate load of cancer cells in the circulation. The quantitative analysis method yields results that are highly correlated with the treatment outcomes of lung cancer patients and serves to predict the treatment outcome in a short time after the treatment is administered.

The method of assessing lung cancer therapy comprises: collecting a body fluid from a subject, extracting total RNA of the body fluid sample, employing qPCR to amplify marker gene transcripts of total RNA for detecting cancer cells in body fluid, and analyzing qPCR threshold cycle number with a set of mathematical formulae.

The present invention further teaches a method to translate expression level of multiple gene transcripts measured by qPCR to the amount of circulating lung cancer cells which is termed cancer cell load (Lc) in this invention.

The present invention further teaches a scoring method and mathematical formulae for calculating cancer cell load, Lc, and predicting lung cancer treatment outcome with the Lc value.

The present invention now will be described more fully hereinafter with reference to the accompanying drawings, which are intended to be read in conjunction with both this summary, the detailed description and any preferred and/or particular embodiments specifically discussed.

BRIEF DESCRIPTION OF THE DRAWINGS

The present invention will become apparent upon reading the following detailed description of the present invention in conjunction with the drawings, as follows.

DETAILED DESCRIPTION OF THE INVENTION

Figure 1:
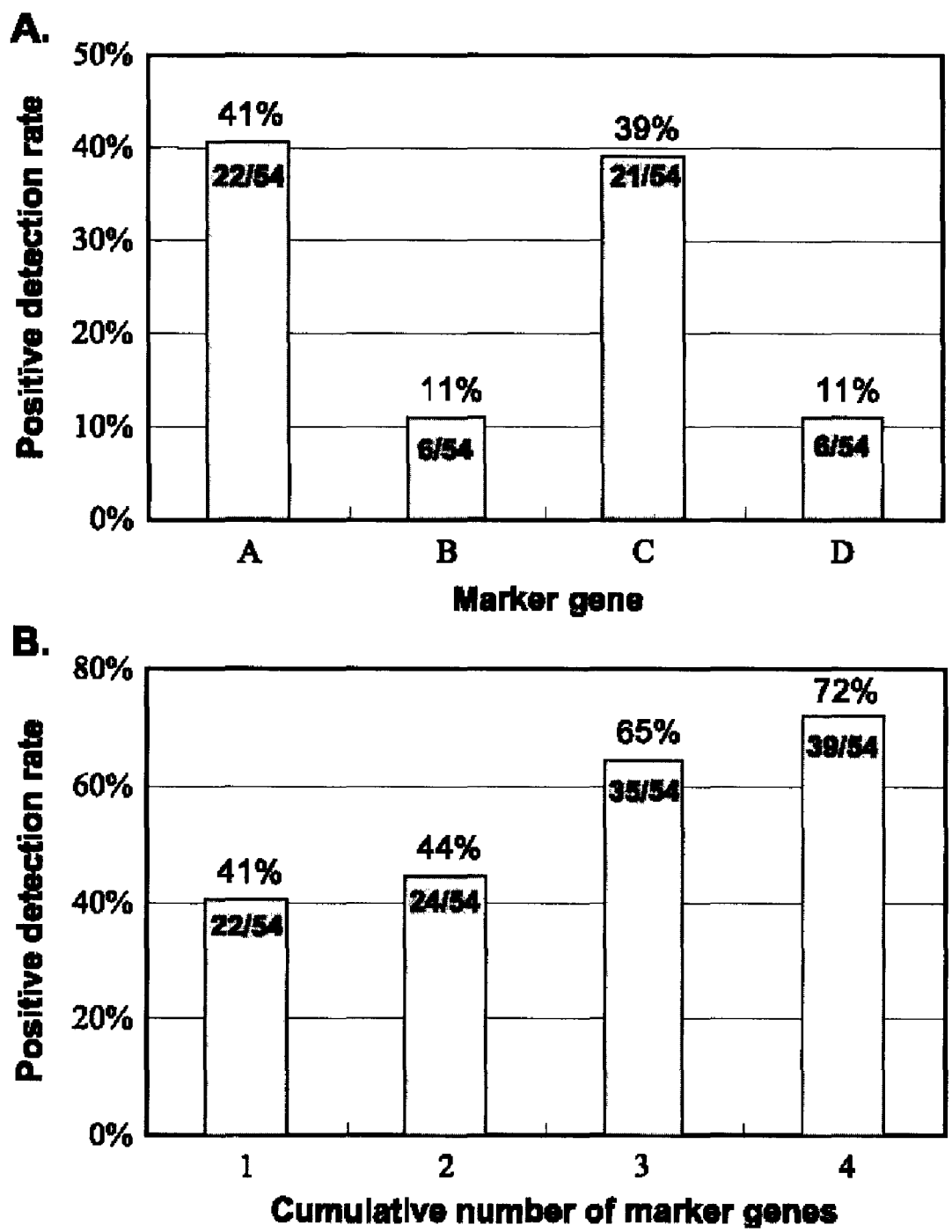
FIG. 1 shows the analysis of positive detection rates with a panel of 4 marker genes. A, positive detection rate for the individual four marker genes. B, positive detection rate increases with the number of marker genes used in the assay.

The present invention is directed to a method for lung cancer therapy assessment and a method of cancer relapse detection. Unlike current imaging assessment methods, the present invention provides a rapid assessment that uses multiple marker genes in qPCR assay for detecting circulating lung cancer cells in body fluids.

Compared with immunohistology and flow cytometry assessment methods, the present invention requires no additional antibody antigen interaction process. Extra molecular recognition process reduces the detection rate. Compared with the RT-PCR detection method for circulating cancer cell in prior art, using a panel of marker genes instead of a single marker gene improves the detection rate. On the other hand, it is not trivial to quantitatively analyze and integrate the expression level of multiple transcripts in a qPCR assay and correlating the analysis results to predict treatment outcome. The present invention teaches a set of mathematical formulae which yield results well correlated with lung cancer treatment outcome.

The multiple marker genes that may be selected include, but are not limited to, keratin 19 (KRT19), ubiquitin thiolesterase (UCHL1), Highly similar to HSFIB1 for fibronectin, and tripartite motif-containing 28 (TRIM28).

The method of the present invention for rapid lung cancer therapy efficacy assessment comprises the following steps:

collecting a body fluid sample from a human subject;
extracting total RNA from said body fluid sample;
amplifying a panel of gene transcripts of said total RNA by qPCR;
measuring the expression level of each gene transcript in said panel of gene transcripts of said total RNA from a number of healthy controls and lung cancer patients, wherein a qPCR threshold cycle number is used to represent the expression level of the gene transcripts;
deriving a reference threshold score using the qPCR threshold cycle numbers of the gene transcripts in the panel measured for healthy controls and lung cancer patients;
calculating an indicative score using the qPCR threshold cycle numbers of the gene transcripts in the panel measured for a lung cancer patient both before and after therapy; and
determining therapy efficacy by comparing the indicative scores obtained before and after therapy.

The formulae used in this invention to calculate the values in these steps can be found in the section "Quantitative Analysis (Scoring) of the PCR Results" below.

In the present invention, the body fluids are collected from, but not limit to, peripheral blood or pleural effusion.

In the present invention, the number of multiple gene transcripts selected for amplification is more than two.

In the present invention, the nucleic acid extraction is done without prior antibody/antigen interaction or other molecular recognition processes to isolate cancer cells from normal blood cells.

In the present invention, the quantitative analysis for therapy efficacy is performed as early as one day after the therapeutic regimen is administered.

The method of the present invention for cancer relapse detection comprises the following steps:

collecting a body fluid sample from a human subject;
extracting total RNA from said body fluid sample;
amplifying a panel of gene transcripts of said total RNA by qPCR;
measuring the expression level of each gene transcript in said panel of gene transcripts of said total RNA from a number of healthy controls and lung cancer patients, wherein a qPCR threshold cycle number is used to represent the expression level of the gene transcripts;
deriving a reference threshold score using the qPCR threshold cycle numbers of the gene transcripts in the panel measured for healthy controls and lung cancer patients;
calculating an indicative score using the qPCR threshold cycle numbers of the gene transcripts in the panel measured for a lung cancer patient; and
determining the presence of circulating lung cancer cells by comparing the indicative scores with the reference threshold score.

Without further elaboration, it is believed that one skilled in the art can, using the preceding description, utilize the present invention to its fullest extent. The practice of the present invention will employ, unless otherwise indicated, conventional techniques of cell biology, molecular biology, and biochemistry which are within the skill of the art. Such techniques are explained fully in the literature. The following examples are, therefore, to be considered as merely illustrative, and not limitative of the remainder of the disclosure in any way.

Materials and Methods

Patients and Specimens

Peripheral blood samples were obtained with informed consent from 54 patients with histologically documented NSCLC in the National Taiwan University Hospital. Staging procedures included chest radiography, bronchoscopy, brain and thoracic computed tomography, sonography, and bone scintigraphy. The follow-up period of the lung cancer patients was up to 85 months for stage I patients who were still alive in May 2003. The normal control population consisted of 24 healthy volunteers with no history or present diagnosis of malignancy. Among the 54 patients, 32 were men and 22 were women with median age of 65 years (SD=11, range=28-81). In the healthy control group, 16 were men and 8 were women with median age of 57.5 years (SD=15.1, range=27-78). Adenocarcinoma lung cancer cell lines (A549, CL3, H928, CL1-0, CL1-5, CRL-5865, CRL-5806, and CRL-5807) and squamous carcinoma lung cancer cell lines (NCl-H520, H2981, CRL-5802, and HTB-54) were used to validate the candidate markers and for analyzing the correlation between Lc value and cancer cell number.

Sample Collection and RNA Preparation

The blood sample collection and RNA preparation methods were the same as described by Peck et al. (Peck, Cancer Res. 58:2761-2765, 1998) Briefly, two samples were collected from each subject with Vacutainers (Becton Dickinson, Rutherford, N.J.). The first tube with 1 to 2 mL of peripheral blood was discarded and only the second tube with 3 to 4 mL of blood was assayed to avoid epithelial cell contamination by the needle when it pierced through the skin. Total RNA was extracted with the QIAamp RNA Blood Mini kit (Qiagen, Hiden, Germany) within 2 hours after the blood samples were collected.

Identification of Candidate Marker Genes

To take advantage of the vast information of the expressed sequence tags databases generated with cancer cell lines, we used the cDNA Digital Gene Expression Displayer developed by the Cancer Genome Anatomy Project (Strausberg, J. Pathol, 195:31-40, 2001) to identify genes that were differentially expressed between lung cancer cells and leukocytes. The Digital Gene Expression Displayer program identified differentially expressed genes among 47,036 sequences in five lung cancer cDNA libraries and 21,460 sequences in six leukocyte cDNA libraries with a P filter set at 0.01. The differentially expressed genes were ranked by sequence odds ratio. The genes with the highest sequence odds ratios were selected as candidate marker genes for quantitative PCR (qPCR) assay. The in silico Digital Gene Expression Displayer program search of the National Cancer Institute-Cancer Genome Anatomy Project database yielded 85 overexpressed genes with a sequence odds ratio >16 between the lung cancer cDNA libraries and the leukocyte cDNA libraries. These candidate genes were further verified by real-time quantitative PCR (qPCR). All of the cancer cell lines are listed as above and pooled and peripheral blood mononuclear cells from 12 healthy controls were used as samples in the first round verification. Fifty-nine candidate marker genes showed >2-fold differential expression ratios, but only 19 genes had differential expression ratios >100,000. Marker genes with large differential expression ratios are required to detect rare circulating cancer cells in blood samples containing millions of peripheral blood mononuclear cells. By using qPCR to detect the presence of 19 candidate genes in the clinical specimens of 54 NSCLC patients and 24 normal controls, four marker genes including KRT19 were identified to show positive detection in at least two NSCLC patients. The four marker genes are listed in Table 1.

The first three marker genes had negligible expression in the blood samples of normal controls by the qPCR assay and are labeled as genes A to C. The fourth gene, labeled as gene D, had high expression in the cancer patient group versus the normal control group, but had residual expression in normal peripheral blood mononuclear cells. Therefore, the present invention sets the positive detection threshold at 99% confidence interval in the normal control group to avoid false positive detection.

TABLE 1

List of a panel of four marker genes

| Gene | Title | Genbank Accession Nos. | GeneID |
|---|---|---|---|
| A | keratin 19 (KRT19) | NM_002276 | 3880 |
| B | ubiquitin thiolesterase (UCHL1) | NM_004181 | 7345 |
| C | Highly similar to HSFIB1 for fibronectin | NM_054034 | 2335 |
| D | tripartite motif-containing 28 (TRIM28) | NM_005762 | 10155 |

```
GenBank accession no NM_002276.3 (SEQ ID NO:1)

1 cgcccctgac accattcctc ccttcccccc tccaccggcc gcgggcataa aaggcgccag 61 gtgagggcct cgccgctcct cccgcgaatc gcagcttctg agaccagggt tgctccgtcc 121 gtgctccgcc tcgccatgac ttcctacagc tatcgccagt cgtcggccac gtcgtccttc 181 ggaggcctgg gcggcggctc cgtgcgtttt gggccggggg tcgcctttcg cgcgcccagc 241 attcacgggg gctccggcgg ccgcggcgta tccgtgtcct ccgcccgctt tgtgtcctcg 301 tcctcctcgg gggcctacgg cggcggctac ggcggcgtcc tgaccgcgtc cgacgggctg 361 ctggcgggca acgagAAGCT AACCATGCAG AACCTCAACG ACCGCctggc ctcctacctg 421 gacaaggtgc gcgccctgga ggcggccaac ggcgagctag aggtgaagat ccgcgactgg 481 taccagaagc aggggcctgg gcccTCCCGC GACTACAGCC ACTACTACAC GACCatccag 541 gacctgcggg acaagattct tggtgccacc attgagaact ccaggattgt cctgcagatc 601 gacaatgccc gtctggctgc agatgacttc cgaaccaagt ttgagacgga acaggctctg 661 cgcatgagcg tggaggccga catcaacggc ctgcgcaggg tgctggatga gctgaccctg 721 gccaggaccg acctggagat gcagatcgaa ggcctgaagg aagagctggc ctacctgaag
```

-continued

```
 781 aagaaccatg aggaggaaat cagtacgctg aggggccaag tgggaggcca ggtcagtgtg 841 gaggtggatt ccgctccggg caccgatctc gccaagatcc tgagtgacat gcgaagccaa 901 tatgaggtca tggccgagca gaaccggaag gatgctgaag cctggttcac cagccggact 961 gaagaattga accgggaggt cgctggccac acggagcagc tccagatgag caggtccgag 1021 gttactgacc tgcggcgcac ccttcagggt cttgagattg agctgcagtc acagctgagc 1081 atgaaagctg ccttggaaga cacactggca gaaacggagg cgcgctttgg agcccagctg 1141 gcgcatatcc aggcgctgat cagcggtatt gaagcccagc tgggcgatgt gcgagctgat 1201 agtgagcggc agaatcagga gtaccagcgg ctcatggaca tcaagtcgcg gctggagcag 1261 gagattgcca cctaccgcag cctgctcgag ggacaggaag atcactacaa caatttgtct 1321 gcctccaagg tcctctgagg cagcaggctc tggggcttct gctgtccttt ggagggtgtc 1381 ttctgggtag agggatggga aggaagggac ccttacccccc ggctcttctc ctgacctgcc

1441 aataaaaatt tatggtccaa gggaaaaaaa aaaaaaaaa aaaaaaaaaa aaaaaaaaa 1501 aaaaaaaaaa aaa
```

GenBank accession no NM_004181.3 (SEQ ID NO:2)

```
   1 cctgggcggc tccgctagct gttttttcgtc ttccctaggc tatttctgcc gggcgctccg 61 cgaagatgca gctcaagccg atggagatca accccgagat gctgaacaaa gtgctgtccc 121 ggctgggggt cgccggccag tggcgcttcg tggacgtgct ggggctggaa gaggagtctc 181 tgggctcggt gccagcgcct gcctgcgcgc tgctgctgct gtttcccctc acggcccagc 241 atgagaactt caggaaaaag cagattgaag agctgaaggg acaagaagtt agtcctaaag 301 tgtacttcat gaagcagacc attgggaatt cctgtggcaC AATCGGACTT ATTCACGCAg 361 tggccaataa tcaagacaaa ctgggatttg aggatggatc agttctgaaa cagtttcttt 421 ctgaaacaga gaaatgtccc ctgaagaca gagcaaaatg ctttgaaaag aatgaggcca 481 tacaggcagc ccatgatgcc gtggcacagg aaggccaatg tcgggtagat gacaaggtga 541 atttccattt tattctgttt aacaacgtgg atggccacct ctatgaactt gatggacgaa 601 tgccttttcc ggtgaaccat ggcgccagtt cagaggacac cctgctgaag gacgctgcca 661 aggtcTGCAG AGAATTCACC GAGcgtgagc aaggagaagt ccgcttctct gccgtggctc 721 tctgcaaggc agcctaatgc tctgtgggag ggactttgct gatttcccct cttcccttca 781 acatgaaaat atataccccc ccatgcagtc taaaatgctt cagtacttgt gaaacacagc 841 tgttcttctg ttctgcagac acgccttccc ctcagccaca cccaggcact taagcacaag 901 cagagtgcac agctgtccac tgggccattg tggtgtgagc ttcagatggt gaagcattct 961 ccccagtgta tgtcttgtat ccgatatcta acgctttaaa tggctactttt ggtttctgtc 1021 tgtaagttaa gaccttggat gtggtttaat tgtctgtcct caaaaggaat aaaacttttc 1081 tgctgataag ataaaaaaaa aaaaaaaaa
```

GenBank accession no NM_054034.2 (SEQ ID NO:3)

```
   1 gcccgcgccg gctgtgctgc acaggggag gagagggaac cccaggcgcg agcgggaaga 61 ggggacctgc agccacaact tctctggtcc tctgcatccc ttctgtccct ccacccgtcc 121 ccttccccac cctctggccc ccaccttctt ggaggcgaca accccgggaa ggcattagaa 181 gggattttc ccgcaggttg cgaagggaag caaacttggt ggcaacttgc ctcccggtgc 241 gggcgtctct cccccaccgt ctcaacatgc ttagggtcc ggggcccggg ctgctgctgc 301 tggccgtcca gtgcctgggg acagcggtgc cctccacggg agcctcgaag agcaagaggc
```

-continued

```
 361 aggctcagca aatggttcag ccccagtccc cggtggctgt cagtcaaagc aagcccggtt
 421 gttatgacaa tggaaaacac tatcagataa atcaacagtg ggagcggacc tacctaggca
 481 atgcgttggt ttgtacttgt tatggaggaa gccgaggttt taactgcgag agtaaacctg
 541 aagctgaaga gacttgcttt gacaagtaca ctgggaacac ttaccgagtg ggtgacactt
 601 atgagcgtcc taaagactcc atgatctggg actgtacctg catcggggct gggcgaggga
 661 gaataagctg taccatcgca aaccgctgcc atgaaggggg tcagtcctac aagattggtg
 721 acacctggag gagaccacat gagactggtg gttacatgtt agagtgtgtg tgtcttggta
 781 atggaaaagg agaatggacc tgcaagccca tagctgagaa gtgttttgat catgctgctg
 841 ggacttccta tgtggtcgga gaaacgtggg agaagcccta ccaaggctgg atgatggtag
 901 attgtacttg cctgggagaa ggcagcggac gcatcacttg cacttctaga aatagatgca
 961 acgatcagga cacaaggaca tcctatagaa ttggagacac ctggagcaag aaggataatc
1021 gaggaaaacct gctccagtgc atctgcacag gcaacggccg aggagagtgg aagtgtgaga
1081 ggcacacctc tgtgcagacc acatcgagcg gatctggccc cttcaccgat gttcgtgcag
1141 ctgtttacca accgcagcct cacccccagc ctcctcccta tggccactgt gtcacagaca
1201 gtggtgtggt ctactctgtg gggatgcagt ggctgaagac acaaggaaat aagcaaatgc
1261 tttgcacgtg cctgggcaac ggagtcagct gccaagagac agctgtaacc cagacttacg
1321 gtggcaactc aaatggagag ccatgtgtct taccattcac ctacaatggc aggacgttct
1381 actcctgcac cacagaaggg cgacaggacg gacatctttg gtgcagcaca acttcgaatt
1441 atgagcagga ccagaaatac tctttctgca cagaccacac tgttttggtt cagactcgag
1501 gaggaaattc caatggtgcc ttgtgccact tccccttcct atacaacaac cacaattaca
1561 ctgattgcac ttctgagggc agaagagaca acatgaagtg gtgtgggacc acacagaact
1621 atgatgccga ccagaagttt gggttctgcc ccatggctgc ccacgaggaa atctgcacaa
1681 ccaatgaagg ggtcatgtac cGCATTGGAG ATCAGTGGGA Taagcagcat gacatgggtc
1741 acATGATGAG GTGCACGTGT GTtgggaatg gtcgtgggga atggacatgc attgcctact
1801 cgcagcttcg agatcagtgc attgttgatg acatcactta caatgtgaac gacacattcc
1861 acaagcgtca tgaagagggg cacatgctga actgtacatg cttcggtcag ggtcggggca
1921 ggtgaagtg tgatcccgtc gaccaatgcc aggattcaga gactgggacg ttttatcaaa
1981 ttggagattc atgggagaag tatgtgcatg gtgccagata ccagtgctac tgctatggcc
2041 gtggcattgg ggagtggcat tgccaacctt tacagaccta tccaagctca agtggtcctg
2101 tcgaagtatt tatcactgag actccgagtc agcccaactc ccacccatc cagtggaatg
2161 caccacagcc atctcacatt tccaagtaca ttcccaggtg gagacctgtg agtatcccac
2221 ccagaaacct tggatactga gtctcctaat cttatcaatt ctgatggttt ctttttttcc
2281 cagcttttga gccaacaact ctgattaact attcctatag catttactat atttgtttag
2341 tgaacaaaca atatgtggtc aattaaattg actcgtagac tgaaaaaaaa aaaaaaaaa
2401 aa
```

GenRank accession no NM_005762.2 (SEQ ID NO:4)

```
   1 ggcgcgcggg cgagcggttg tgcttgtgct tgtggcgcgt ggtgcgggtt tcggcggcgg
  61 ctgaggaaga agcgcgggcg gcgccttcgg gaggcgagca ggcagcagtt ggccgtgccg
 121 tagcagcgtc ccgcgcgcgg cgggcagcgg cccaggaggc gcgtggcggc gctcggcctc
 181 gcggcggcgg cggcggcagc ggcccagcag ttggcggcga gcgcgtctgc gcctgcgcgg
```

-continued

```
 241 cgggccccgc gccccteete ccecectggg cgecceeggc ggegtgtgaa tggeggeete
 301 cgcggcggca gcctcggcag cagcggcctc ggccgcctct ggcagcccgg cccgggcga
 361 gggctccgct ggcggcgaaa agcgctccac cgccccttcg gccgcagcct cggcctctgc
 421 ctcagccgcg cgtcgtcgc ccgcgggggg cggcgccgag cgctggagc tgctggagca
 481 ctgcggcgtg tgcagagagc gcctgcgacc cgagagggag ccccgcctgc tgccctgttt
 541 gcactcggcc tgtagtgcct gcttagggcc cgcggcccc ccgccgcca acagctcggg
 601 ggacggcggg gcggcgggcg acggcaccgt ggtggactgt cccgtgtgca agcaacagtg
 661 cttctccaaa gacatcgtgg agaattattt catgcgtgat agtggcagca aggctgccac
 721 cgacgcccag gatgcgaacc agtgctgcac tagctgtgag gataatgccc cagccaccag
 781 ctactgtgtg gagtgctcgg agcctctgtg tgagacctgt gtagaggcgc accagcgggt
 841 gaagtacacc aaggaccata ctgtgcgctc taccgggcca gccaagtctc gggatggtga
 901 acgtactgtc tattgcaacg tacacaagca tgaaccccct tgtgctgttt tgtgagagctg
 961 tgatactctc acctgccgag actgccagct caacgcccac aaggaccacc agtaccagtt
1021 cttagaggat gcagtgagga accagcgcaa gctcctggcc tcactggtga agcgccttgg
1081 ggacaaacat gcaacattgc agaagagcac caaggaggtt cgcagctcaa tccgccaggt
1141 gtctgacgta cagaagcgtg tgcaagtgga tgtcaagatg ccatcctgc agatcatgaa
1201 ggagctgaat aagcggggcc gtgtgctggt caatgatgcc cagaaggtga ctgaggggca
1261 gcaggagcgc ctggagcggc agcactggca catgaccaag atccagaagc accaggagca
1321 cattctgcgc tttgcctctt gggctctgga gagcgacaac aacacagccc ttttgctttc
1381 taagaagttg atctacttcc agctgcaccg ggccctcaag atgattgtgg atcccgtgga
1441 gccacatggc gagatgaagt ttcagtggga cctcaatgcc tggaccaaga gtgccgaggc
1501 ctttggcaag attgtggcag agcgtcctgg cactaactca acaggccctg cacccatggc
1561 ccctccaaga gccccagggc ccctgagcaa gcagggctct ggcagcagcc agcccatgga
1621 ggtgcaggaa ggctatggct ttgggtcagg agatgatccc tactcaagtg cagagcccca
1681 tgtgtcaggt gtgaaacggt cccgctcagg tgagggcgag gtgagcggcc ttatgcgcaa
1741 ggtgccacga gtgagccttg aacgcctgga cctggacctc acagctgaca gccagccacc
1801 cgtcttcaag gtcttcccag gcagtaccac tgaggactac aaccttattg ttattgaacg
1861 tggcgctgcc gctgcagcta ccggccagcc agggactgcg cctgcaggaa ccctggtgc
1921 cccacccctg gctggcatgg ccattgtcaa ggaggaggag acggaggctg ccattggagc
1981 ccctcctact gccactgagg gccctgagac caaacctgtg cttatggctc ttgcggaggg
2041 tcctggtgct gagggtcccc gcctggcctc acctagtggc agcaccagct cagggctgga
2101 ggtggtggct cctgagggta cctcagcccc aggtggtggc ccgggaaccc tggatgacag
2161 tgccaccatt tgccgtgtct gccagaagcc aggcgatctg gttatgtgca accagtgtga
2221 gttttgtttc cacctggact gtcacctgcc ggccctgcag gatgtaccag gggaggagtg
2281 gagctgctca ctctgccatg tgctccctga cctgaaggag gaggatggca gcctcagcct
2341 ggatggtgca gacagcactg gcgtggtggc caagctctca ccagccaacc agcggaaATG
2401 TGAGCGTGTA CTGCTGGccc tattctgtca cgaaccctgc cgccccctgc atcagctggc
2461 taccgactcc accttctccc tggaccagcc cggtggcacc ctggatctga ccctgatccg
2521 tgcccgcctc caggagaagt tgtcacctcc ctacagctcc ccacaggagt ttgcccagga
2581 tgtgggccgc atgttcaagc aattcaacaa gttaactgag gacaaggcag acgtgcagtc
```

```
-continued
2641  catcatcggc  ctgcagcgct  tcttcgagac  gcgcatgaac  gaggccttcg  gtgacaccaa 2701  gttctctgct  gtgctggtgg  agcccccgcc  gatgagcctg  cctggtgctg  gcctgagttc 2761  ccaggagctg  tctggtggcc  ctggtgatgg  ccctgaggc   tggagccccc  atggccagcc 2821  cagcctggct  ctgttctctg  tcctgtcacc  ccatccccac  tcccctggtg  gcctgactcc 2881  cactccctgg  tggcccatc   ccccagttcc  tcacgatatg  gtttttactt  ctgtggattt 2941  aataaaaact  tcaccagtta  aaaaaaaaaa  aaaaaaaaaa  aaaaaaaaa
```

Quantitative PCR Assay

To detect a few cancer cells in the circulation, a highly sensitive PCR amplification is necessary. cDNA was derived from 1 to 2 μg of total RNA by random primed reverse transcription, and nested PCR was used to amplify the candidate marker gene transcripts for detection. The primer sets for qPCR amplification are listed in Table 1 of U.S. Provisional Application No. 60/596,104, filed Sep. 1, 2005, from which priority benefit is claimed by this application and which is incorporated herein. The first round (outer) of the nested PCR was done using 1 μL of 20-fold diluted cDNA with a PCR mixture containing 0.1 μmol/L outer primer pair, 0.2 mmol/L deoxynucleotide triphosphate, 50 mmol/L Tris-HCl (pH 8.3), 10 mmol/L KCl, 5 mmol/L $(NH_4)_2SO_4$, 2 mmol/L $MgCl_2$, and 0.75 units of FastStart Taq DNA polymerase (Roche, Mannheim, Germany) in a total volume of 12.5 μL. The PCR conditions were one cycle at 94° C. for 7 minutes followed by 25 cycles at 94° C. for 50 seconds, 60° C. for 50 seconds, 72° C. for 35 seconds, and a final extension at 72° C. for 10 minutes.

For the second round (inner) of the nested PCR amplification, quantitative measurement was performed with qPCR assay. The reaction mixture contained 2 μL of the first round PCR product, 0.25 μmol/L inner primers, and SYBR Green PCR master mix (Applied Biosystems, Foster City, Calif.) in a total volume of 20 μL. The qPCR assays were done with an ABI prism 7000 SDS (Applied Biosystems) instrument. The qPCR condition was 95° C. for 10 minutes followed by 40 cycles at 95° C. for 15 seconds, 60° C. for 25 seconds, and 72° C. for 35 seconds.

Quantitative Analysis (Scoring) of the PCR Results

By using a qPCR instrument, the threshold cycle ($C_T$), the fractional cycle number at which the SYBR Green I fluorescence exceeded a set level above baseline, was determined. We used GAPDH mRNA as an internal control. The relative amount of mRNA, normalized against the GAPDH mRNA, was expressed as $\Delta C_T = C_T^{(GAPDH)} - C_T^{(marker\ gene)}$. If the fluorescence signal was undetected after 40 cycles, the $C_T$ value was given the maximum cycle number of 40 for analysis convenience. The differential expression ratio of a candidate marker gene, Q, for patients versus normal controls was calculated by $Q = 2^{\Delta C_T - mean\ of\ \Delta C_T^{in\ normal}}$. To estimate the number of circulating cancer cells, we normalized the differential expression ratio of each marker gene to take into account the different amount of the marker gene transcripts in cancer cells. We then summed up the expression ratios of the marker genes to estimate the cancer cell load in the circulation in a semi-quantitative way. Cancer cells and their gene expression profiles are heterogeneous in individuals. To take the heterogeneity of gene expression in different patients into account, the expression of marker genes need to be normalized among test subjects. The formula for normalizing the expression ratio, $E_{ij}$, of a marker gene is $E_{ij} = (Q_{ij} - Q_j)/\sigma_j$, where i is the patient index, j is the marker gene index, $Q_{ij}$ is the differential expression ratio of marker gene j in patient i, $Q_j$ is the mean and $\sigma_j$ is the standard deviation (SD) of the expression ratios of the 54 patients for marker gene j. The load of cancer cells, Lc, in the circulation of a patient is defined as $Lc = \Sigma E_j$ where n is the number of marker genes. In this study, the load of cancer cell, Lc, is used as an indicative score for the amount of circulating cancer cells. The value of Lc ranged between −2.2 and 8.4.

Statistical Analysis

Fisher's exact test and Student's t test were used to compare the clinicopathologic characteristics of patients with low and high Lc values. All statistical tests were two sided. Survival time of the patients was calculated from the day of specimen collection. Survival curves were obtained by the Kaplan-Meier method. The difference of survival times between two groups was analyzed with the log-rank test. $P < 0.05$ was considered statistically significant.

EMBODIMENT 1 ENHANCEMENT OF POSITIVE DETECTION RATE WITH MULTIPLE MARKER GENES

As shown in FIG. 1A, the positive detection rate of circulating cancer cells in NSCLC patients was 41%, 11%, 39%, and 11% for genes A to D, respectively. The fractions of positives among all the patients are indicated in the columns.

Increasing the number of marker genes raised the positive detection rate for NSCLC patients to 72% (39 of 54) compared with 41% (22 of 54) positive detection rate using the KRT19 marker gene alone (FIG. 1B). These results prove that using multiple markers indeed improves the positive detection rate. The B marker gene was not detected in squamous cell lung cancer patients, but the other three genes were detected in patients with adenocarcinoma or squamous cell carcinoma.

EMBODIMENT 2 CIRCULATING CANCER CELL LOAD AND PATIENT OUTCOME

To investigate the correlation between the number of circulating cancer cells and patient outcome, the present invention used cancer cell load Lc (see MATERIALS AND METHODS) as a measure to indicate the number of cancer cells in circulation.

Figure 2:
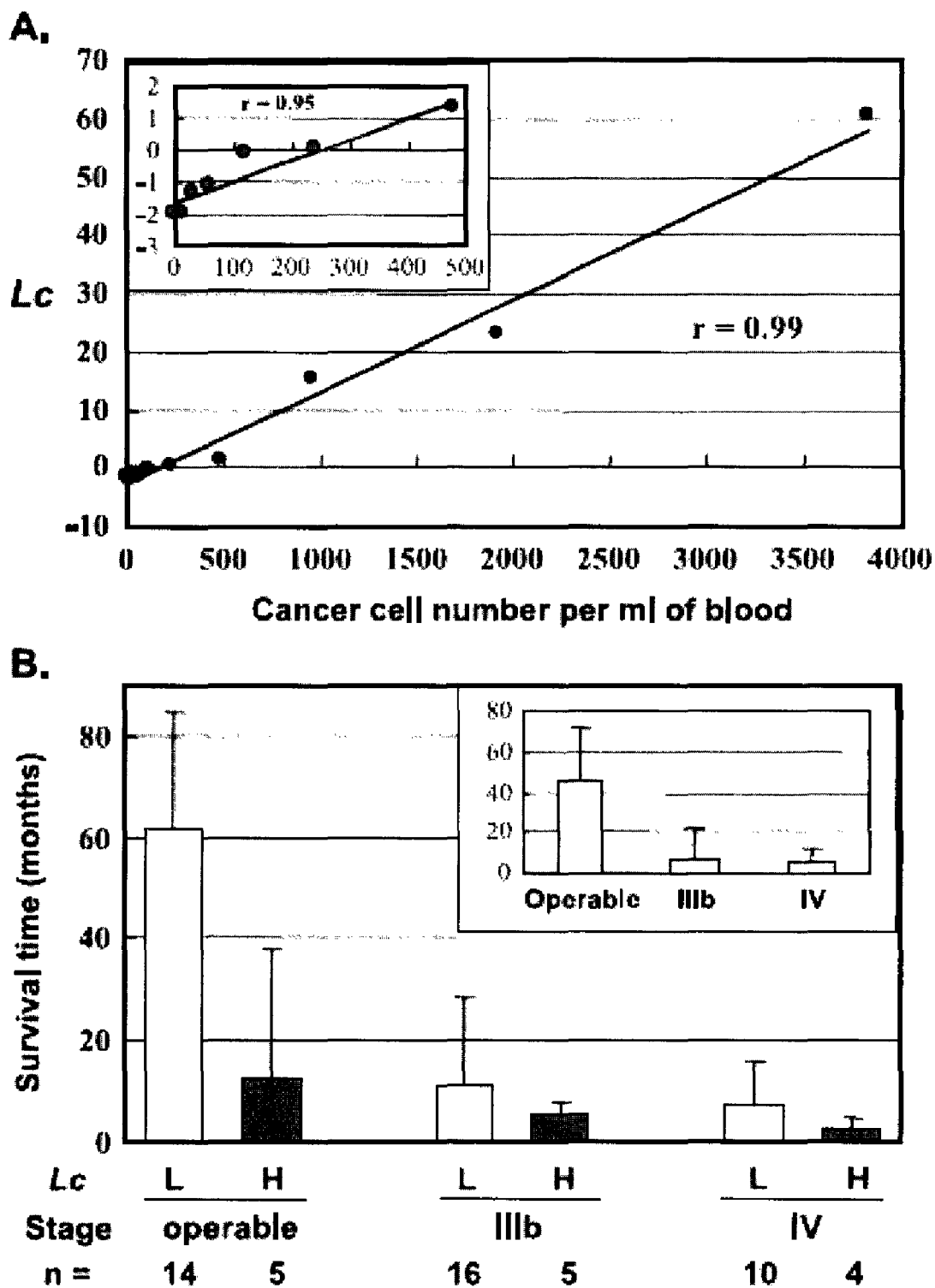
FIG. 2 shows the correlation of Lc value with the concentration of cancer cell number in peripheral blood. A, plot to show that Lc value is linearly correlated with the number of circulating cancer cells. Inset, Lc value versus the number of cancer cells between 0 and 480 cells/mL of peripheral blood. B, median survival time for patients of various TNM stages and with high ($\geq$1) or low (<1) Lc values. Inset, survival time of patient classified by the TNM staging method. Bars, standard deviation (SD).

By definition, Lc increases with the number of circulating cells. The correlation between the number of circulating cancer cells and Lc values can be determined by spiking different numbers of lung cancer cells (CL1-0) into peripheral blood mononuclear cells (FIG. 2A). The present invention shows a good correlation (r=0.99) between cancer cell number and Lc value.

Figure 3:
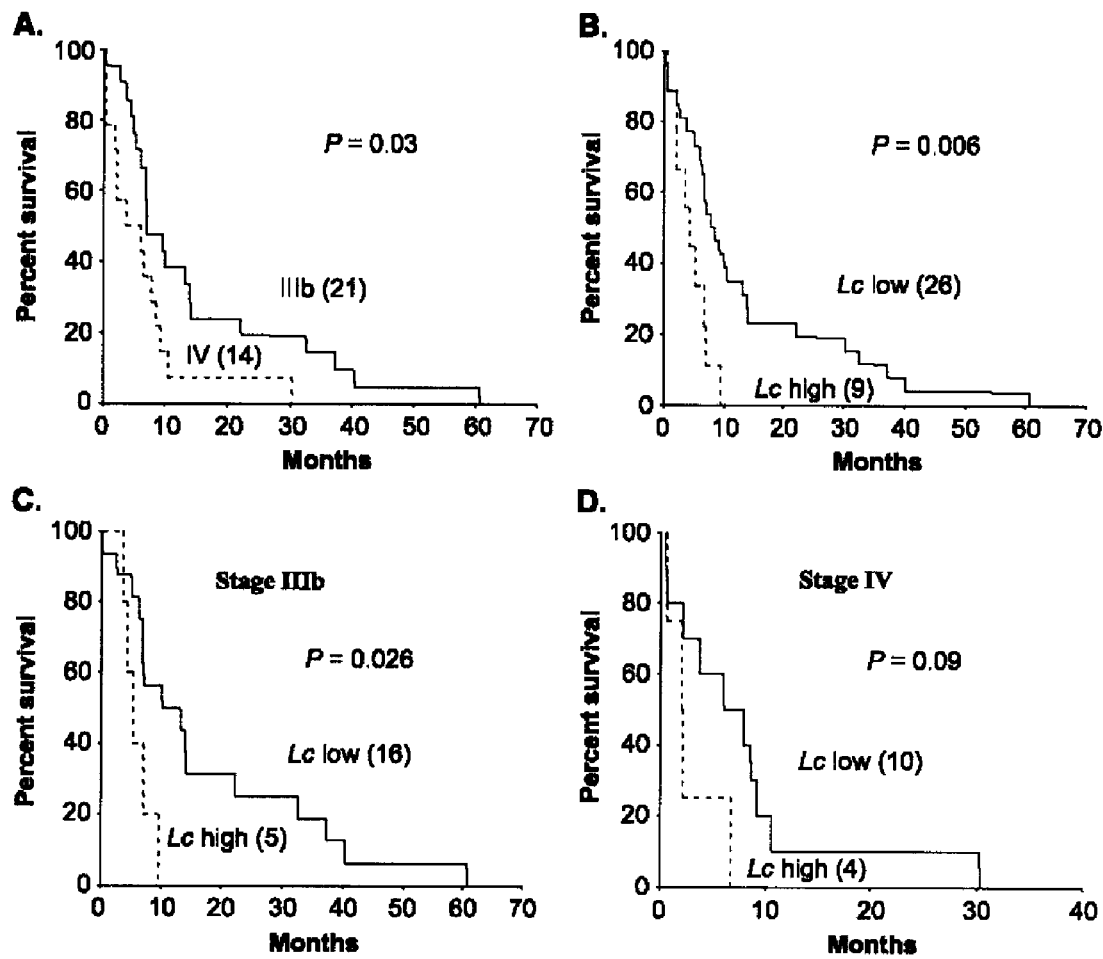
FIG. 3 shows the survival analysis of late stage patients with high ($\geq$1) or low (<1) Lc values. A, Kaplan-Meier survival plots of late TNM stage patients (IIIb and IV). B, Kaplan-Meier survival plots for the same late stage patients grouped by the Lc value. C, Kaplan-Meier survival plots for the stage IIIb patients grouped by the Lc value. D, Kaplan-Meier survival plots for the stage IV patients grouped by the Lc value.

The data shown in FIGS. 2B and 3 indicate that patients of the same stage who had higher Lc had worse outcomes. The results indicate that Lc measurement is a supplementary tool to the traditional TNM staging method to better predict the outcome of cancer patients.

To determine whether Lc can be used as an indicator of patient outcome, the present invention analyzed the Lc value versus the survival time of stage I to IIIa patients who received surgical resection. We found that patients who survived for more than 5 years had Lc values less than 1. Therefore, we set Lc=1 as the reference threshold score for the subsequent prognosis studies in the 54 lung cancer patients. The study divided the patients at different stages into two groups (Lc≧1 or Lc<1) and examined their survival time. As expected, late-stage patients had shorter survival times than did early-stage patients (FIG. 2B, inset). The cancer load (Lc) study further distinguished that for patients of the same stage, those with low Lc had longer survival time than those with high Lc value (FIG. 2B). For the operable early-stage patients, the survival time is highly correlated (P=0.002) with Lc value. The Lc value was then used to analyze the prognosis of late-stage patients (stages IIIb and IV) with Kaplan-Meier survival plots. The survival time difference was more significant by using Lc as a classification parameter (FIG. 3B, P=0.006) than by using the traditional TNM classification (FIG. 3A, P=0.03). The number of patients in each group is shown in parentheses in the figures. We further used the Lc parameter to divide the patients of the same stage into low (Lc<1) and high (Lc≧1) value groups and examined the survival plots. The survival time of stage IIIb patients with low and high Lc value was significantly different (FIG. 3C, P=0.026). The same analysis on stage IV patients did not achieve statistical significance (FIG. 3D, P=0.09). These prognosis studies establish using Lc=1 as the reference threshold score for detecting the presence of circulating lung cancer cells.

Using the four marker genes and setting the reference threshold score to 1, the positive detection rates of patients with circulating cancer cells were 67% (4 of 6) for stage I, 100% (4 of 4) for stage II, 67% (6 of 9) for stage IIIa, 67% (14 of 21) for stage IIIb, and 79% (11 of 14) for stage IV. The detection rate indicates the sensitivity of using the four markers for detecting the presence of circulating NSCLC cells.

EMBODIMENT 3 ASSESSMENT OF THERAPY EFFICACY

Figure 4:
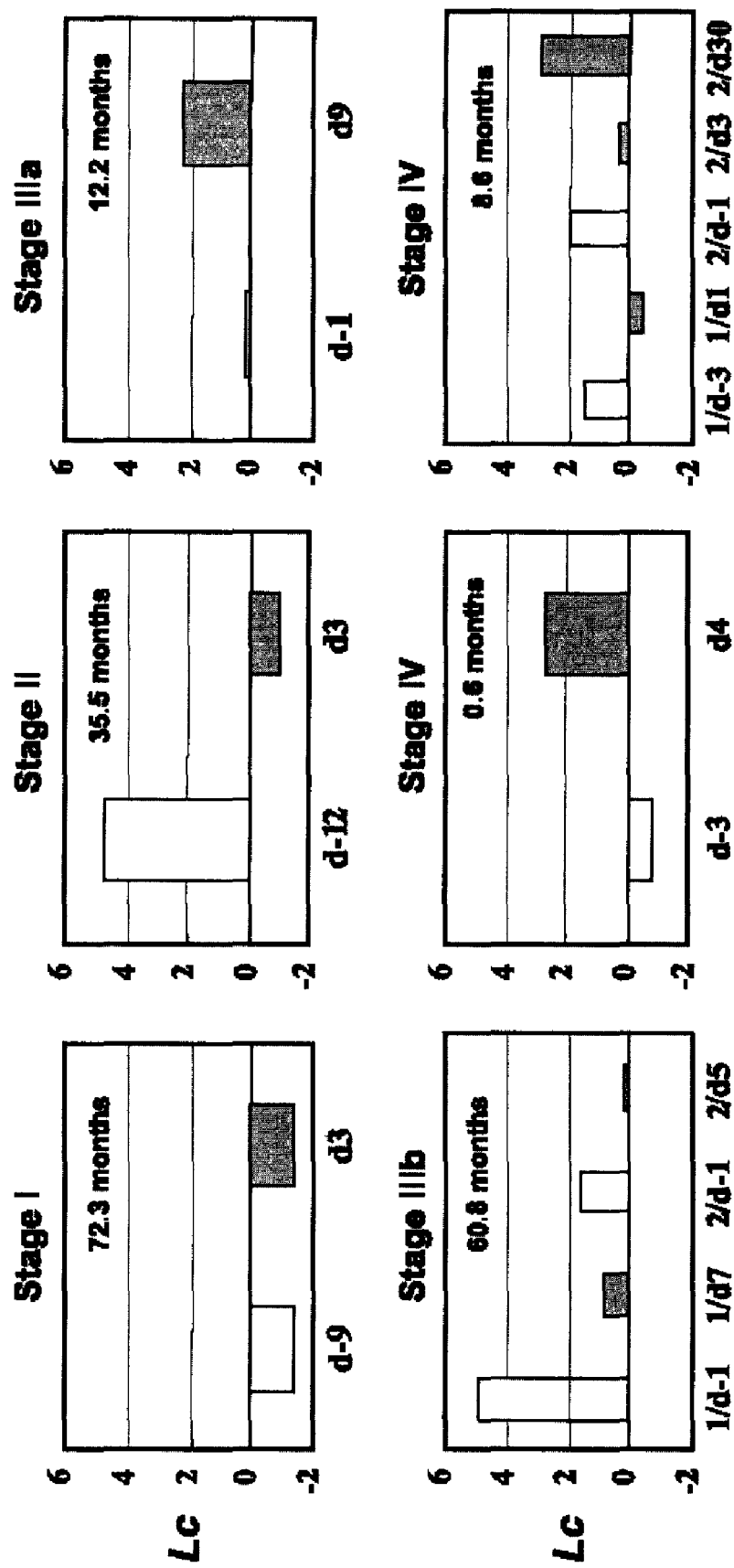
FIG. 4 shows lung cancer therapy efficacy assessment with circulating cancer cell detection for six different NSCLC patients. Median survival time of each patient is indicated in the figure panels. The designations for the treatment and sampling day are described in the text.

FIG. 4 shows the assessment of six patients before and after therapy. The stage I, II, and IIIa patients received surgical resection, whereas the stage IIIb and IV patients received chemotherapy. "d–n" indicates that the samples were collected n days before therapy, "dn" indicates that the samples were collected on the nth day after therapy, and "n/" indicates the course number of chemotherapy. The stage I patient had negative Lc values before and after treatment and was still alive on the last follow-up date (72.3 months). The Lc values decreased for the stage II and IIIb patients after therapy. The stage IIIa and IV patients had higher Lc values after the last course of treatment and had short survival times. These results suggest that measurement of the cancer cell load, Lc, can be used to reveal whether therapy is efficacious.

EMBODIMENT 4 RELAPSE DETECTION

In FIG. 4 the stage IIIb patient's treatment was efficacious and the Lc value decreased after the first treatment. However, the Lc value went back up to exceed 1 and the patient was given a second course of treatment on the next day. The second treatment for the stage IIIb was assessed to be effective by the method disclosed in this invention on the fifth day after the treatment. The survival time was 60.8 months for the patient. The last example in FIG. 4 was a stage IV patient. The Lc value decreased on the second day of the treatment. The Lc value of the patient went up again to exceed 1 in a follow-up examination and a second treatment was given on the next day. However, the second treatment failed to completely eradicate the cancer cells and the Lc value kept rising with time. The patient had a survival time of 8.6 months.

TABLE 2

Clinicopathologic characteristics and their correlation with Lc value of NSCLC patients

| Characteristic | Lc | | P |
| --- | --- | --- | --- |
| | Low | High | |
| Age (y), mean ± SD | 63.6 ± 10.5 | 61.3 ± 13.0 | 0.549* |
| Gender, no. patients | | | |
| Male | 20 | 20 | 0.03 |
| Female | 20 | 2 | |
| Smoking, no. patients | | | |
| No | 24 | 7 | 0.546 |
| Yes | 16 | 7 | |
| Histology, no. patients | | | |
| Adenocarcinoma | 25 | 10 | 0.442 |
| Squamous cell carcinoma | 12 | 2 | |
| Poorly differentiated | 3 | 2 | |
| Stage† | | | |
| I-IIIa | 14 | 5 | 1.0 |
| IIIb-IV | 26 | 9 | |

*Derived with Student's t test; other Ps were derived with Fisher's exact test. All statistical tests were two-sided.
†Tumor stage was classified according to the International System for Staging Lung Cancer.

The percentage of patients with high Lc value is greater for the late-stage patients than for the early-stage patients except for the stage II patients. The invention study looked into this issue and found that the markers have different detection rates for different histologic types of NSCLC. The markers are more sensitive for detecting squamous carcinoma (85.7%; 12 of 14) compared with adenocarcinomas (68.6%; 24 of 35) and others (60%, 3 of 5). An investigation on the histologic types of the NSCLC patients revealed that the available stage II patients were composed of three (75%) squamous carcinoma and one (25%) adenocarcinoma patients, whereas the other stage patients were composed of 11% to 33% squamous carcinoma, 50% to 71% adenocarcinoma, and 5% to 22% poorly differentiated cell type patients. The higher detection rate of the stage II patients can therefore be attributed to the limited number of clinical samples and their histologic composition.

The data shows that detection of circulating cancer cells is a valid supplement to the TNM method for better cancer staging. The two methods combined together provide better information for designing lung cancer treatment strategies. In the study of this invention, the 5-year survival rate of early-stage (I-IIIa) NSCLC patients was 30% to 50% after surgical resection. This invention teaches a more precise staging method by including detection of circulating cancer cells to aid in deciding whether adjuvant therapeutic regimens in addition to tumor resection are beneficial to the patients.

At present, a reliable serologic biomarker assay for assessing the treatment response of NSCLC patients is not available. Two courses of chemotherapy are traditionally given before imaging is done to evaluate the treatment response of NSCLC patients. It showed in lung cancer patients that the Lc could be used for monitoring therapeutic response and relapse. Because different cancer cell types have different levels of marker gene expression, patients with higher Lc values do not necessarily have more circulating cancer cells in their peripheral blood than do patients with lower Lc values. Nevertheless, the semiquantitative approach is useful for measuring the relative cancer cell load in a patient's peripheral blood to monitor the effectiveness of treatment. The present method highlights an alternative approach to rapidly assess the treatment response of NSCLC patients. Compared with imaging methods which take weeks to detect the change of tumor size for therapy efficacy assessment, the invention teaches a method capable of assessing therapy efficacy on the next day of treatment as shown in FIG. 4. The method of the present invention may therefore help to design more comprehensive and reasonable therapeutic regimens at earlier dates for NSCLC patients.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for lung cancer therapy assessment comprising:

(a) collecting a blood or pleural effusion sample from a human subject with lung cancer;

(b) extracting total RNA of said sample;

(c) amplifying a panel of gene transcripts of said total RNA by qPCR, wherein said panel of gene transcripts, named j, comprises keratin 19 (KRT19), ubiquitin thiolesterase (UCHL1), tripartite motif-containing 28 (TRIM28), and Highly similar to HSFIB1 for fibronectin;

(d) measuring a qPCR threshold cycle number $(C_T)_j$ for each gene transcript of j in said panel of gene transcripts of said total RNA from said sample, and a qPCR threshold cycle number $C_T^{(GAPDH)}$ for the control gene transcript of said total RNA from said sample;

(e) calculating a differential expression ratio $Q_j$ for each gene transcript of j in said panel of gene transcripts of said total RNA according to $Q_j = 2^{(\Delta C_T)_j - (\Delta C_T)_{j,mean}}$ wherein $(\Delta C_T)_j = C_T^{(GAPDH)} - (C_T)_j$, and $(\Delta C_T)_{j, mean}$ is a predetermined mean of $(\Delta C_T)_j$ for gene transcript of j over a population of persons not inflicted with lung cancer;

(f) calculating a normalized expression ratio $E_j$ for each gene transcript of j in said panel of gene transcripts of said total RNA according to $E_j = (Q_j - Q_{j,mean})/\sigma_j$ wherein $Q_{j, mean}$ is a predetermined mean of differential expression ratio for gene transcript of j over a population of lung cancer patients and $\sigma_j$ is a predetermined standard deviation of differential expression ratio for gene transcript of j over said population of lung cancer patients;

(g) calculating a load of cancer cells (Lc) according to

Lc=$\Sigma E_j$, where the summation is over all the gene transcripts in said panel of gene transcripts;

(h) administering a therapy for lung cancer to said human subject with lung cancer;

(i) performing steps (a) to (g) to yield a load of cancer cells (Lc) for said human subject after said therapy for lung cancer; and (j) comparing said Lc before and after administering said therapy, wherein the therapy is determined to be effective if Lc after the therapy is less than a predetermined value, or is determined to be not effective if Lc after the therapy is not less than the predetermined value.

2. A method of claim 1, wherein efficacy of said therapy is determined as in step (j) within at least one day after said therapy is administered.

* * * * *

SEQUENCE LISTING

```
<160> NUMBER OF SEQ ID NOS: 4

<210> SEQ ID NO 1
<211> LENGTH: 1513
<212> TYPE: DNA
<213> ORGANISM: Homo sapiens

<400> SEQUENCE: 1 cgccctgac   accattcctc   ccttccccc    tccaccggcc   gcgggcataa   aaggcgccag      60
gtgagggcct  cgccgctcct  cccgcgaatc   gcagcttctg   agaccagggt   tgctccgtcc     120
gtgctccgcc  tcgccatgac  ttcctacagc   tatcgccagt   cgtcggccac   gtcgtccttc     180
ggaggcctgg  gcggcggctc  cgtgcgtttt   gggccggggg   tcgcctttcg   cgcgcccagc     240
attcacgggg  gctccggcgg  ccgcggcgta   tccgtgtcct   ccgcccgctt   tgtgtcctcg     300
tcctcctcgg  gggcctacgg  cggcggctac   ggcggcgtcc   tgaccgcgtc   cgacgggctg     360
ctggcgggca  acgagaagct  aaccatgcag   aacctcaacg   accgcctggc   ctcctacctg     420
gacaaggtgc  gcgccctgga  ggcggccaac   ggcgagctag   aggtgaagat   ccgcgactgg     480
taccagaagc  aggggcctgg  gccctcccgc   gactacagcc   actactacac   gaccatccag     540
gacctgcggg  acaagattct  tggtgccacc   attgagaact   ccaggattgt   cctgcagatc     600
gacaatgccc  gtctggctgc  agatgacttc   cgaaccaagt   ttgagacgga   acaggctctg     660
cgcatgagcg  tggaggccga  catcaacggc   ctgcgcaggg   tgctggatga   gctgaccctg     720
gccaggaccg  acctggagat  gcagatcgaa   ggcctgaagg   aagagctggc   ctacctgaag     780
aagaaccatg  aggaggaaat  cagtacgctg   aggggccaag   tgggaggcca   ggtcagtgtg     840
gaggtggatt  ccgctccggg  caccgatctc   gccaagatcc   tgagtgacat   gcgaagccaa     900
tatgaggtca  tggccgagca  gaaccggaag   gatgctgaag   cctggttcac   cagccggact     960
gaagaattga  accgggaggt  cgctggccac   acggagcagc   tccagatgag   caggtccgag    1020
gttactgacc  tgcggcgcac  ccttcagggt   cttgagattg   agctgcagtc   acagctgagc    1080
atgaaagctg  ccttggaaga  cacactggca   gaaacggagg   cgcgctttgg   agcccagctg    1140
gcgcatatcc  aggcgctgat  cagcggtatt   gaagcccagc   tgggcgatgt   gcgagctgat    1200
agtgagcggc  agaatcagga  gtaccagcgg   ctcatggaca   tcaagtcgcg   gctggagcag    1260
gagattgcca  cctaccgcag  cctgctcgag   ggacaggaag   atcactacaa   caatttgtct    1320
gcctccaagg  tcctctgagg  cagcaggctc   tggggcttct   gctgtccttt   ggagggtgtc    1380
```

```
ttctgggtag agggatggga aggaagggac ccttaccccc ggctcttctc ctgacctgcc    1440
aataaaaatt tatggtccaa gggaaaaaaa aaaaaaaaaa aaaaaaaaaa aaaaaaaaaa    1500
aaaaaaaaaa aaa                                                      1513

<210> SEQ ID NO 2
<211> LENGTH: 1110
<212> TYPE: DNA
<213> ORGANISM: Homo sapiens

<400> SEQUENCE: 2
cctgggcggc tccgctagct gttttcgtc ttccctaggc tatttctgcc gggcgctccg      60
cgaagatgca gctcaagccg atggagatca accccgagat gctgaacaaa gtgctgtccc    120
ggctgggggt cgccggccag tggcgcttcg tggacgtgct ggggctggaa gaggagtctc    180
tgggctcggt gccagcgcct gcctgcgcgc tgctgctgct gtttcccctc acggcccagc    240
atgagaactt caggaaaaag cagattgaag agctgaaggg acaagaagtt agtcctaaag    300
tgtacttcat gaagcagacc attgggaatt cctgtggcac aatcggactt attcacgcag    360
tggccaataa tcaagacaaa ctgggatttg aggatggatc agttctgaaa cagtttcttt    420
ctgaaacaga gaaatgtcc cctgaagaca gagcaaaatg ctttgaaaag aatgaggcca    480
tacaggcagc ccatgatgcc gtggcacagg aaggccaatg tcgggtagat gacaaggtga    540
atttccattt tattctgttt aacaacgtgg atggccacct ctatgaactt gatggacgaa    600
tgccttttcc ggtgaaccat ggcgccagtt cagaggacac cctgctgaag gacgctgcca    660
aggtctgcag agaattcacc gagcgtgagc aaggagaagt ccgcttctct gccgtggctc    720
tctgcaaggc agcctaatgc tctgtgggag ggactttgct gatttcccct cttcccttca    780
acatgaaaat atatacccc ccatgcagtc taaaatgctt cagtacttgt gaaacacagc    840
tgttcttctg ttctgcagac acgccttccc ctcagccaca cccaggcact taagcacaag    900
cagagtgcac agctgtccac tgggccattg tggtgtgagc ttcagatggt gaagcattct    960
ccccagtgta tgtcttgtat ccgatatcta acgctttaaa tggctacttt ggtttctgtc   1020
tgtaagttaa gaccttggat gtggtttaat tgtttgtcct caaaaggaat aaaacttttc   1080
tgctgataag ataaaaaaaa aaaaaaaaaa                                    1110

<210> SEQ ID NO 3
<211> LENGTH: 2402
<212> TYPE: DNA
<213> ORGANISM: Homo sapiens

<400> SEQUENCE: 3
gcccgcgccg gctgtgctgc acaggggggag gagagggaac cccaggcgcg agcgggaaga     60
ggggacctgc agccacaact tctctggtcc tctgcatccc ttctgtccct ccacccgtcc    120
ccttccccac cctctggccc ccaccttctt ggaggcgaca accccgggga ggcattagaa    180 gggattttc ccgcaggttg cgaagggaag caaacttggt ggcaacttgc ctccggtgc     240 gggcgtctct ccccaccgt ctcaacatgc ttaggggtcc ggggcccggg ctgctgctgc    300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt taactgcgag agtaaacctg    540
```

```
aagctgaaga gacttgcttt gacaagtaca ctgggaacac ttaccgagtg ggtgacactt      600
atgagcgtcc taaagactcc atgatctggg actgtacctg catcggggct gggcgaggga      660
gaataagctg taccatcgca aaccgctgcc atgaaggggg tcagtcctac aagattggtg      720
acacctggag gagaccacat gagactggtg gttacatgtt agagtgtgtg tgtcttggta      780
atggaaaagg agaatggacc tgcaagccca tagctgagaa gtgttttgat catgctgctg      840
ggacttccta tgtggtcgga gaaacgtggg agaagcccta ccaaggctgg atgatggtag      900
attgtacttg cctgggagaa ggcagcggac gcatcacttg cacttctaga aatagatgca      960
acgatcagga cacaaggaca tcctatagaa ttggagacac ctggagcaag aaggataatc     1020
gaggaaacct gctccagtgc atctgcacag caacggccg aggagagtgg aagtgtgaga      1080
ggcacacctc tgtgcagacc acatcgacg gatctggccc cttcaccgat gttcgtgcag      1140
ctgtttacca accgcagcct caccccagc ctcctcccta tggccactgt gtcacagaca      1200
gtggtgtggt ctactctgtg gggatgcagt ggctgaagac acaaggaaat aagcaaatgc     1260
tttgcacgtg cctgggcaac ggagtcagct gccaagagac agctgtaacc cagacttacg     1320
gtggcaactc aaatggagag ccatgtgtct taccattcac ctacaatggc aggacgttct     1380
actcctgcac cacagaaggg cgacaggacg gacatctttg gtgcagcaca acttcgaatt     1440
atgagcagga ccagaaatac tcttttctgca cagaccacac tgttttggtt cagactcgag     1500
gaggaaattc caatggtgcc ttgtgccact tccccttcct atacaacaac cacaattaca     1560
ctgattgcac ttctgagggc agaagagaca acatgaagtg gtgtgggacc acacagaact     1620
atgatgccga ccagaagttt gggttctgcc ccatggctgc ccacgaggaa atctgcacaa     1680
ccaatgaagg ggtcatgtac cgcattggag atcagtggga taagcagcat gacatgggtc     1740
acatgatgag gtgcacgtgt gttgggaatg tcgtgggga atggacatgc attgcctact     1800
cgcagcttcg agatcagtgc attgttgatg acatcactta caatgtgaac gacacattcc     1860
acaagcgtca tgaagagggg cacatgctga actgtacatg cttcggtcag ggtcggggca     1920 ggtgaagtg tgatcccgtc gaccaatgcc aggattcaga gactgggacg ttttatcaaa     1980
ttggagattc atgggagaag tatgtgcatg gtgtcagata ccagtgctac tgctatggcc     2040
gtggcattgg ggagtggcat tgccaacctt tacagaccta tccaagctca gtggtcctg      2100 tcgaagtatt tatcactgag actccgagtc agcccaactc ccaccccatc cagtggaatg     2160
caccacagcc atctcacatt tccaagtaca ttctcaggtg gagacctgtg agtatcccac     2220
ccagaaacct tggatactga gtctcctaat cttatcaatt ctgatggttt cttttttttcc     2280 cagcttttga gccaacaact ctgattaact attcctatag catttactat atttgtttag     2340
tgaacaaaca atatgtggtc aattaaattg acttgtagac tgaaaaaaaa aaaaaaaaaa     2400
aa                                                                    2402

<210> SEQ ID NO 4
<211> LENGTH: 2989
<212> TYPE: DNA
<213> ORGANISM: Homo sapiens

<400> SEQUENCE: 4
ggcgcgcggg cgagcggttg tgcttgtgct tgtggcgcgt ggtgcgggtt tcggcggcgg       60
ctgaggaaga agcgcgggcg gcgccttcgg gaggcgagca ggcagcagtt ggccgtgccg      120
tagcagcgtc ccgcgcgcgg cgggcagcgg cccaggaggc gcgtggcggc gctcggcctc      180
gcggcggcgg cggcggcagc ggcccagcag ttggcggcga gcgcgtctgc gcctgcgcgg      240
```

```
cgggccccgc gccccctcctc ccccccctggg cgccccccggc ggcgtgtgaa tggcggcctc      300
cgcggcggca gcctcggcag cagcggcctc ggccgcctct ggcagcccgg gcccgggcga      360
gggctccgct ggcggcgaaa agcgctccac cgccccttcg gccgcagcct cggcctctgc      420
ctcagccgcg gcgtcgtcgc ccgcggggggg cggcgccgag gcgctggagc tgctggagca      480
ctgcggcgtg tgcagagagc gcctgcgacc cgagagggag ccccgcctgc tgccctgttt      540
gcactcggcc tgtagtgcct gcttagggcc cgcggccccc gccgccgcca acagctcggg      600
ggacggcggg gcggcgggcg acggcaccgt ggtggactgt cccgtgtgca agcaacagtg      660
cttctccaaa gacatcgtgg agaattattt catgcgtgat agtggcagca aggctgccac      720
cgacgcccag gatgcgaacc agtgctgcac tagctgtgag gataatgccc cagccaccag      780
ctactgtgtg gagtgctcgg agcctctgtg tgagacctgt gtagaggcgc accagcgggt      840
gaagtacacc aaggaccata ctgtgcgctc tactgggcca gccaagtctc gggatggtga      900
acgtactgtc tattgcaacg tacacaagca tgaacccctt gtgctgtttt gtgagagctg      960
tgatactctc acctgccgag actgccagct caatgcccac aaggaccacc agtaccagtt     1020
cttagaggat gcagtgagga accagcgcaa gctcctggcc tcactggtga agcgccttgg     1080
ggacaaacat gcaacattgc agaagagcac caaggaggtt cgcagctcaa tccgccaggt     1140
gtctgacgta cagaagcgtg tgcaagtgga tgtcaagatg ccatcctgc agatcatgaa      1200
ggagctgaat aagcggggcc gtgtgctggt caatgatgcc cagaaggtga ctgaggggca     1260
gcaggagcgc ctggagcggc agcactgac catgaccaag atccagaagc caggagca       1320
cattctgcgc tttgcctctt gggctctgga gagtgacaac aacacagccc ttttgctttc     1380
taagaagttg atctacttcc agctgcaccg ggccctcaag atgattgtgg atcccgtgga     1440
gccacatggc gagatgaagt ttcagtggga cctcaatgcc tggaccaaga gtgccgaggc     1500
cttttggcaag attgtggcag agcgtcctgg cactaactca acaggccctg cacccatggc     1560
ccctccaaga gccccagggc ccctgagcaa gcagggctct ggcagcagcc agcccatgga     1620
ggtgcaggaa ggctatggct ttgggtcagg agatgatccc tactcaagtg cagagcccca     1680
tgtgtcaggt gtgaaacggt cccgctcagg tgagggcgag gtgagcggcc ttatgcgcaa     1740
ggtgccacga gtgagccttg aacgcctgga cctggacctc acagctgaca gccagccacc     1800
cgtcttcaag gtcttcccag gcagtaccac tgaggactac aaccttattg ttattgaacg     1860
tggcgctgcc gctgcagcta ccggccagcc agggactgcg cctgcaggaa cccctggtgc     1920
cccaccctg gctggcatgg ccattgtcaa ggaggaggag acggaggctg ccattggagc     1980
ccctcctact gccactgagg gccctgagac caaacctgtg cttatggctc ttgcggaggg     2040
tcctggtgct gagggtcccc gcctggcctc acctagtggc agcaccagct cagggctgga     2100
ggtggtggct cctgagggta cctcagcccc aggtggtggc ccgggaaccc tggatgacag     2160
tgccaccatt tgccgtgtct gccagaagcc aggcgatctg gttatgtgca accagtgtga     2220
gttttgtttc cacctggact gtcacctgcc ggccctgcag gatgtaccag ggaggagtg     2280
gagctgctca ctctgccatg tgctccctga cctgaaggag gaggatggca gcctcagcct     2340
ggatggtgca gacagcactg gcgtggtggc caagctctca ccagccaacc agcggaaatg     2400
tgagcgtgta ctgctggccc tattctgtca cgaaccctgc cgccccctgc atcagctggc     2460
taccgactcc accttctccc tggaccagcc cggtggcacc ctggatctga ccctgatccg     2520
tgcccgcctc caggagaagt tgtcacctcc ctacagctcc ccacaggagt ttgcccagga     2580
```

-continued

```
tgtgggccgc atgttcaagc aattcaacaa gttaactgag gacaaggcag acgtgcagtc    2640
catcatcggc ctgcagcgct tcttcgagac gcgcatgaac gaggccttcg gtgacaccaa    2700
gttctctgct gtgctggtgg agcccccgcc gatgagcctg cctggtgctg gcctgagttc    2760
ccaggagctg tctggtggcc ctggtgatgg ccctgaggc tggagccccc atggccagcc     2820
cagcctggct ctgttctctg tcctgtcacc ccatcccac tccctggtg gcctgactcc      2880 cactccctgg tggccccatc ccccagttcc tcacgatatg gtttttactt ctgtggattt    2940
aataaaaact tcaccagtta aaaaaaaaaa aaaaaaaaa aaaaaaaa                  2989
```